United States Patent
Jagirdar et al.

(10) Patent No.: US 11,342,076 B1
(45) Date of Patent: May 24, 2022

(54) MONITORING PATIENT'S HEALTH

(71) Applicant: Qure.ai Technologies Private Limited, Mumbai (IN)

(72) Inventors: Ammar Jagirdar, Mumbai (IN); Adlon Pereira, Mumbai (IN); Pradeep Kumar Thummala, Ukkunagaram Visakhapatnam (IN); Arun Kant Sharma, Jaipur (IN); Vijay Senapathi, Whitefie (IN); Anshul Chauhan, Kurukshetra (IN)

(73) Assignee: QURE.AI TECHNOLOGIES PRIVATE LIMITED, Mumbai (IN)

( * ) Notice: Subject to any disclaimer, the term of this patent is extended or adjusted under 35 U.S.C. 154(b) by 0 days.

(21) Appl. No.: 17/499,946

(22) Filed: Oct. 13, 2021

(30) Foreign Application Priority Data

Aug. 27, 2021 (IN) .............................. 202121038904

(51) Int. Cl.
*G16H 50/20* (2018.01)
*G16H 10/20* (2018.01)
(Continued)

(52) U.S. Cl.
CPC ........... *G16H 50/20* (2018.01); *G06F 40/279* (2020.01); *G16H 10/20* (2018.01); *G16H 10/60* (2018.01);
(Continued)

(58) Field of Classification Search
None
See application file for complete search history.

(56) References Cited

U.S. PATENT DOCUMENTS 9,491,277 B2 * 11/2016 Vincent .................. H04W 4/90
2010/0235295 A1 * 9/2010 Zides ................. G06Q 30/0282
705/347

(Continued)

FOREIGN PATENT DOCUMENTS

WO WO-2008042988 A1 * 4/2008 ............. G06Q 30/02
WO 2020087014 A1 4/2020

OTHER PUBLICATIONS

Sandeep Reddy, John Fox & Maulik P Purohit, Artificial Intelligence-enabled healthcare delivery, 112 Journal of the Royal Society of Medicine 22-28 (2018) (Year: 2018).*

(Continued)

*Primary Examiner* — John P Go
*Assistant Examiner* — Nicholas Akogyeram, II
(74) *Attorney, Agent, or Firm* — Shumaker, Loop & Kendrick, LLP (57) ABSTRACT

Disclosed is a system and a method for monitoring patient's health. Data associated with multiple questions nudged to a patient may be received. A plurality of symptoms may be extracted. The plurality of symptoms may be analyzed using to generate a health assessment score. The health assessment score may be compared with a predefined threshold to determine a health condition. A deviation in the health condition may be determined by comparing the health condition and previous health data. A risk level may be identified using an artificial intelligence technique. A course of action may be recommended to the patient in real-time based on the risk level and the health condition. A healthcare practitioner may be identified in real-time. The healthcare practitioner and the patient may be notified in real-time. A follow-up check for the patient may be scheduled based on the risk level and the health condition.

9 Claims, 4 Drawing Sheets

(51) Int. Cl.
*G16H 50/70* (2018.01)
*G16H 20/10* (2018.01)
*G16H 40/20* (2018.01)
*G16H 10/60* (2018.01)
*G16H 50/30* (2018.01)
*G06F 40/279* (2020.01)

(52) U.S. Cl.
CPC ............. *G16H 20/10* (2018.01); *G16H 40/20* (2018.01); *G16H 50/30* (2018.01); *G16H 50/70* (2018.01)

(56) References Cited

U.S. PATENT DOCUMENTS

| | | | | |
|---|---|---|---|---|
| 2014/0122109 A1* | 5/2014 | Ghanbari | ............... | G16H 10/20 705/2 |
| 2015/0100326 A1* | 4/2015 | Kowalkiewicz | ....... | G06Q 10/06 705/2 |
| 2015/0288797 A1* | 10/2015 | Vincent | ................... | H04W 4/90 455/404.2 |
| 2015/0379212 A1* | 12/2015 | Kaukab | ................. | G16H 40/20 705/3 |
| 2016/0132652 A1* | 5/2016 | Chapman Bates | .... | G16H 50/80 706/11 |
| 2017/0262604 A1* | 9/2017 | Francois | ................ | G16H 10/60 |
| 2020/0126651 A1 | 4/2020 | Hismatullin | | |
| 2020/0357494 A1* | 11/2020 | Kadri | ..................... | G16H 50/30 |

OTHER PUBLICATIONS

Indian Patent Application No. 202141018779, filed Apr. 23, 2021 and Published on Apr. 30, 2021 as Publication No. 18/2021 entitled An Artifical Intelligence Based Automated Medical Chatbot System for Preliminary Medical Data Enquiry Using Question Answer Model, pp. 1-8.

* cited by examiner

FIGURE 4

MONITORING PATIENT'S HEALTH

TECHNICAL FIELD

The present subject matter described herein, in general, relates to a system and a method for monitoring patient's health. More particularly, to monitoring patient's health using a virtual triage service.

BACKGROUND

Typically, a spread of disease can occur through different pathways. Specifically, airborne diseases such as Covid-19, chickenpox, tuberculosis spread rapidly. In one aspect, a person with some severe symptoms can be a medium to spread the disease. In such case, it is risky for a patient with low immunity to come in contact with the person having severe symptoms. If the patient visits the doctor, there is a high chance of getting infected with the airborne disease. At times, the doctor suggests follow-up checkup date to the patient. However, it may not be possible for the patient to visit doctor frequently due to the risk of getting infected. It must be noted that such visits to the doctor may be dangerous and risky.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for monitoring patient's health. This summary is not intended to identify essential features of the claimed subject matter nor is it intended for use in determining or limiting the scope of the claimed subject matter.

In one implementation, a method for monitoring patient's health is disclosed. Initially, a patient may be nudged with multiple questions on a chat platform. In one aspect, the multiple questions may be nudged dynamically. The multiple questions may be present in multiple languages. The nudge may be generated based on a trained data model. Further, data from the patient may be received. The data may correspond to answers associated with the multiple questions asked to the patient. The data may be received periodically. Further, a plurality of symptoms associated with a health of the patient may be extracted using a Natural language processing technique on the data. Furthermore, a health assessment score of the patient may be generated based on an analysis of the plurality of symptoms using the trained data model. In one aspect, the health assessment score may be compared with a predefined threshold associated with a set of health conditions in order to determine a health condition of the patient. The health condition may correspond to a disease. Subsequently, a deviation in the health condition may be determined based on comparing the health condition and previous health data of the patient. The previous health data may be stored in the trained data model. Upon determining the deviation, a risk level associated with the health condition may be identified using an artificial intelligence technique. The risk level may be identified based on the deviation and the plurality of symptoms. In one aspect, the risk level may be one of a high risk, a low risk and a moderate risk.

Further, a course of action may be recommended to the patient in real-time based on the risk level and the health condition. In one aspect, the course of action may comprise a visit to a health practitioner, and treatment or medicine for the health condition of the patient. Upon recommending the course of action, the healthcare practitioner may be identified in real-time. In one aspect, the healthcare practitioner may be identified based on a demographic profile, the health condition, the risk level, a location of patient, a location of the healthcare practitioner, a distance between the patient and the healthcare practitioner, a traffic condition and a feedback associated with the health care practitioner received from a set of patients. Further, the healthcare practitioner and the patient may be notified in real-time based on the risk level and the deviation. Finally, a follow-up check for the patient may be scheduled based on the risk level and the health condition. The follow-up check may be scheduled in a predefined time period, thereby monitoring patient's health.

In another implementation, a non-transitory computer readable medium embodying a program executable in a computing device for monitoring patient's health is disclosed. The program may comprise a program code for nudging multiple questions to a patient on a chat platform. In one aspect, the multiple questions may be nudged dynamically. The multiple questions may be present in multiple languages. The nudge may be generated based on a trained data model. Further, the program may comprise a program code for receiving data from the patient. In one aspect, the data may correspond to answers associated with the multiple questions asked to the patient. The data may be received periodically. Furthermore, the program may comprise a program code for extracting a plurality of symptoms associated with a health of the patient using a Natural language processing technique on the data. Furthermore, the program may comprise a program code for generating a health assessment score of the patient based on an analysis of the plurality of symptoms using the trained data model. In one aspect, the health assessment score may be compared with a predefined threshold associated with a set of health conditions in order to determine a health condition of the patient. The health condition may correspond to a disease. Further, the program may comprise a program code for determining a deviation in the health condition based on comparing the health condition and previous health data of the patient. The previous health data may be stored in the trained data model. Upon determining the deviation, the program may comprise a program code for identifying a risk level associated with the health condition using an artificial intelligence technique. In one aspect, the risk level may be identified based on the deviation and the plurality of symptoms. The risk level may be one of a high risk, a low risk and a moderate risk.

Further, the program may comprise a program code for recommending a course of action to the patient in real-time based on the risk level and the health condition. The course of action may comprise a visit to a health practitioner, and treatment or medicine for the health condition of the patient. Upon recommending the course of action, the program may comprise a program code for identifying the healthcare practitioner in real-time. In one aspect, the healthcare practitioner may be identified based on a demographic profile, the health condition, the risk level, a location of patient, a location of the healthcare practitioner, a distance between the patient and the healthcare practitioner, a traffic condition and a feedback associated with the health care practitioner received from a set of patients. Subsequently, the program may comprise a program code for notifying the healthcare practitioner and the patient in real-time based on the risk level and the deviation. Finally, the program may comprise a program code for scheduling a follow-up check for the patient based on the risk level and the health condition. The follow-up check may be scheduled in a predefined time period, thereby monitoring patient's health.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures, however, the invention is not limited to the specific method and system for monitoring patient's health disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "nudging," "receiving," "extracting," "generating," "determining," "identifying," "recommending," "notifying," "scheduling," and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

The present subject matter discloses a system and a method for monitoring patients' health. Typically, there is a risk of getting infected with an airborne disease when a patient visits a doctor. More importantly, the present invention discloses a cost effective, safe and an automatic process for monitoring patient's health. Initially, a patient may be nudged with multiple questions. Further, data may be received from the patient. The data may correspond to answers associated with the multiple questions asked to the patient. The data may be further analyzed to extract a plurality of symptoms associated with a health of the patient. It may be noted that the plurality of symptoms may be extracted using a Natural Language Processing technique. Furthermore, the plurality of symptoms may be analyzed using artificial intelligence technique to monitor the patient's health.

While aspects of described system and method for monitoring patient's health may be implemented in any number of different computing systems, environments, and/or configurations, the embodiments are described in the context of the following exemplary system.

Figure 1:
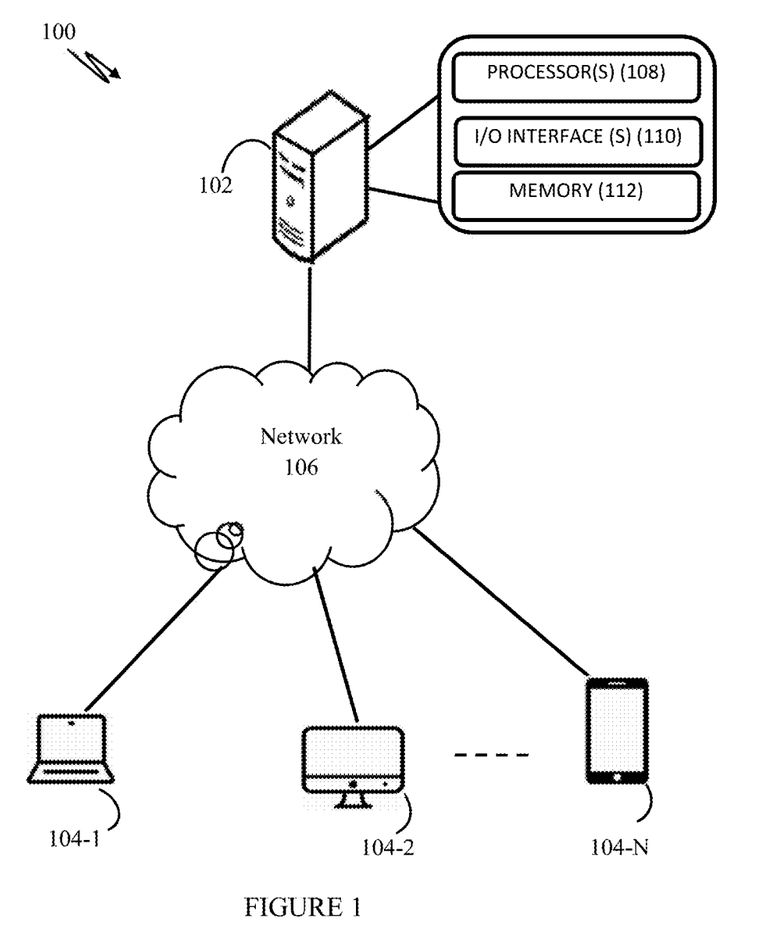
FIG. 1 illustrates a network implementation of a system for monitoring patient's health, in accordance with an embodiment of the present subject matter.

Referring now to FIG. 1, a network implementation 100 of a system 102 for monitoring patient's health is disclosed. It may be noted that one or more users may access the system 102 through one or more user devices 104-1, 104-2, 104-3 . . . 104-N, collectively referred to as user devices 104, hereinafter, or applications residing on the user devices 104. In one aspect, the one or more users may comprise a patient, a patient's relative, a patient's friend and the like.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-2 . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or nonvolatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for monitoring patient's health. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for monitoring patient's health. The system 102 may monitor the patient's health in real-time. The patient's health may be monitored automatically using Natural language processing and Artificial Intelligence technique. In order to monitor the patient's health, initially, the system 102 may nudge multiple questions to a patient. The multiple questions may be nudged on a chat platform. In one aspect, the chat platform may include any social media platform or a chatbot. In another aspect, the system 102 may be integrated with the chat platform.

In one aspect, the patient may be nudged with the multiple questions dynamically. The multiple questions may be present in multiple languages. In other words, the patient may select preferred language on the chat platform. In one example, the question may be—"Has the cough reduced?". In another example, the question may be—"Are you experiencing Fever?". In yet another example, the question may be—"Has any other/new symptom developed over a last night?".

In one aspect, the nudge may be generated based on a trained data model. The trained data model may be a trained machine learning data model. The trained data model may comprise historical data associated with each patient from a set of patients. In one aspect, the set of patients may comprise the patient. The historical data may correspond to previous symptoms, previous disease detected or suffered, follow-ups with doctors, previous health data and the like. In one embodiment, the multiple questions nudged to the patient may be based on the historical data of the patient. It is to be noted that the system 102 may learn from the trained data model to generate the multiple questions in the real time based on patients' profile and medical history.

In one example, consider the patient is diabetic as per the historical data. In the example, the multiple questions may include questions such as—"When did you check your glucose?", "Are you suffering any new symptoms after taking medicines?", "Are you experiencing new symptoms?", and the like. In other words, the multiple questions may include few questions based on the historical data of the patient and a few new questions to check if the patient is facing any other health issue.

Further, the system 102 may receive data from the patient. The data may correspond to answers to the multiple questions nudged to the patient. The data may be received periodically from the patient. In one aspect, once the multiple questions are nudged to the patient, the patient may provide answer to each question. In one example, the answer may be a short answer such as Yes or No. In another example, the answer may be a descriptive answer such as—"I am experiencing fever, body pain and cough".

Upon receiving the data, the system 102 may extract a plurality of symptoms associated with a health of the patient. The plurality of symptoms may be extracted by using a Natural Language Processing technique on the data. In one aspect, the system 102 may analyze the data using the Natural Language Processing technique. Based on the analysis, the system 102 may extract the plurality of symptoms. In one example, the plurality of symptoms may include fever, body pain, cough and the like.

Further, the system 102 may generate a health assessment score for the patient. In one aspect, the plurality of symptoms may be analyzed using the trained data model. Based on the analysis, the health assessment score for the patient may be generated. In one embodiment, the plurality of symptoms may be compared with the historical data associated with the set of patients. Based on the comparison, the system 102 may generate the health assessment score for the patient.

In one embodiment, the system 102 may assign a weightage to each symptom from the plurality of symptoms associated with the patient. The weightage may be assigned based on an analysis of the plurality of symptoms and the trained data model. The weightage may be further used to determine the health assessment score of the patient. In one example, the weightage of fever may be 8, the weightage of cough may be 3, the weightage of body pain may be 9 and the like. In the example, the system 102 may use the weightage of fever, cough and body pain to determine the health assessment score.

Upon determining the health assessment score, the system 102 may determine a health condition of the patient. The health condition may be determined based on comparing the health assessment score with a predefined threshold. The predefined threshold may be associated with a set of health conditions. In one aspect, the health condition may correspond to a disease. In one example, the health condition may include Covid-19, Malaria, Dengue, Diabetes and the like.

In one embodiment, the predefined threshold for each health condition from the set of health conditions may be stored in the trained data model. In one exemplary embodiment, construe the health assessment score of the patient as 13. The predefined threshold for the different health conditions may be 15 for Dengue, 13 for Covid-19 and the like. The system 102 may compare the health assessment score with the predefined threshold of the different health conditions. Based on the comparison, the health condition as Covid-19 may be determined for the patient.

Once the health condition is determined, the system 102 may determine a deviation based on comparing the health condition with previous health data of the patient. The previous health data may be stored in the trained data model. In one embodiment, the deviation may correspond to a change in the symptoms of the patient or a change in the health condition of the patient. The deviation may be a high deviation, a less deviation and a moderate deviation.

In one exemplary embodiment, construe the deviation as the change in symptoms. The change in symptoms may include an increase in fever, an increase in cough, a decrease in an oxygen level and the like. The system 102 may determine the deviation upon comparing the health condition such Covid-19 with the previous health data of the patient.

Further, the system 102 may identify a risk level associated with the health condition. The risk level may be identified based on the deviation and the plurality of symptoms. The risk level may be identified using an Artificial Intelligence (AI) technique. The risk level may indicate a risk of the health condition for the patient. The risk level may be one of a high risk, a low risk and a moderate risk.

In one embodiment, the system 102 may comprise an adaptive risk engine to identify the risk level of the patient. In one example, if the deviation is high, then the risk level may be the high risk. In another example, if the deviation is low, then the risk level may be the low risk.

Upon identifying the risk level, the system 102 may recommend a course of action to the patient. The course of action may be recommended in real-time. The course of action may be recommended based on the risk level and the health condition of the patient. In one aspect, the course of action may comprise a visit to doctor or health practitioner, a treatment or medicine for the health condition of the patient and the like. In other words, the system 102 recommends the patient the next steps to be followed.

In one embodiment, the system 102 may use supervised learning approach to recommend the course of action. The system 102 may learn from past recommendations and actions taken by the patient. The past recommendations and the actions taken by the patient in past may be stored in the trained data model. Based on the learnings, the system 102 may recommend the course of action to the patient.

Further, the system 102 may identify a healthcare practitioner in real-time upon recommending the course of action. The healthcare practitioner may be identified based on a demographic profile of the healthcare practitioner, the health condition of the patient, the risk level, a location of the patient, a location of the healthcare practitioner, a distance between the patient and the healthcare practitioner, a traffic condition, a feedback associated with the healthcare practitioner received from the set of patients and the like. In one aspect, the demographic profile of the health practitioner may include name, age, specialization, city, and the like. In one example, if the feedback associated with the healthcare practitioner received from the set of patients is bad, then the system 102 may identify another healthcare practitioner who is the best suitable for the health condition of the patient.

In one aspect, the healthcare practitioner may be nearest to the patient. In another aspect, the healthcare practitioner may be perfectly suitable for the health condition and the risk level of the patient. In one example, the healthcare practitioner may be a doctor, a nurse, a lab assistant, community health staff and the like.

Once the healthcare practitioner is identified, the system 102 may notify the healthcare practitioner and the patient in real-time. The healthcare practitioner and the patient may be notified based on the risk level and the deviation. It may help to ensure that the healthcare practitioner and the patient are aware of the health condition and the next steps. In one example, the healthcare practitioner and the patient may be notified using a text message. In another example, the healthcare practitioner and the patient may be notified using a phone call.

In one aspect, if the risk level is the low risk and the deviation is less, then the system 102 may recommend medicines to the patient as the course of action. In the aspect, the system 102 may notify the healthcare practitioner and the patient that the medicines are recommended to the patient for a predefined time. In another aspect, the if the risk level is the high risk and the deviation is high, then the system 102 may recommend the visit to the healthcare practitioner as the course of action. In the aspect, the system 102 may notify the healthcare practitioner and the patient that the patient will visit the healthcare practitioner at a defined time.

Further, the system 102 may schedule a follow-up check for the patient. The follow-up check may be scheduled based on the risk level and the health condition. The follow-up check may be scheduled in a predefined period, thereby monitoring patient's health. In one aspect, the follow-up check may be physical follow-up or a remote follow-up. In one example, the predefined time period may be 15 days, 1 month and the like. The predefined time period may vary based on the risk level, the deviation and the health condition of the patient. In one example, if the risk level is the high risk, the system 102 may schedule the follow-up check for the patient. In another example, if the deviation is high, the system 102 may schedule the follow-up check for the patient.

In an aspect, the system 102 may use supervised learning approach to schedule the follow-up. The system 102 may learn from past follow up schedule for the health condition. The past follow-up schedule may be stored in the trained data model. Based on the learnings, the system 102 may schedule the next follow-up for the patient with the similar health conditions.

In one embodiment, the system 102 may monitor the health of the patient using the artificial intelligence and natural language processing techniques. The system 102 may analyze the risk level and the deviation to monitor patient's health. Further, the system 102 may identify a best health practitioner for the patient. Furthermore, the system 102 may schedule a follow-up check for the patient.

In one embodiment, the system 102 may generate an Electronic Medical Record (EMR). The EMR may comprise the data, the health condition, the risk level and the course of action. In other words, the EMR may comprise current data of the patient for a specific time.

In one aspect, the system 102 may track the location of the patient to generate an alert to the set of patients based on the risk level of the patient. The alert may be generated for people living in a predefined area based on the location of the patient. The set of patients may be alerted so that they should not come in contact with the patient. In one example, if the patient is experiencing Covid-19 symptoms. The system 102 may generate the alert to the set of patients based on the location of the patient. The system 102 may send the alert to other people based on the location of the patient. The alert may inform the people that the patient with Covid-19 symptoms is present in their area.

In one embodiment, the system 102 may use a combination of Natural Language Processing techniques to build custom language processing framework. The framework is used for an entity extraction from answers expected from the patient within workflows for multiple diseases. The framework may be designed to be multilingual to handle context across international languages and regional languages. Further, the system 102 may comprise an intent capture mechanism for capturing symptoms relevant for infectious diseases.

In one aspect, the system 102 may comprise a proprietary workflow tool for global clinical experts to modify and adapt infectious disease screening protocols to confirm to latest evidence-based policy. The system 102 may comprise defined workflow with a set of questions for the patient. In one example, the system 102 may comprise evolving the set of questions for the same patient if there is no change in the patient's condition.

In one aspect, the system 102 may comprise allowing the patient to reach out to self-report symptoms. The system 102 may link the disease specific heuristic and map patient conversation to disease timeline.

In one embodiment, the system 102 may comprise an adaptive risk engine to use intent and entity extraction for refining latest risk status received from the patient. The risk engine may be programmed to create schedulers linked to each disease context and follow-up schedules. The follow-up schedules may be the follow-up check for the patient. The risk engine may take into context co-morbidities of the patient to determine follow-up schedules. In one aspect, an output of the risk engine may be of two kinds—(a) a risk class of each patient and an evolving decision tree based on all responses of the patient taken into context, and (b) the latest response given a higher weight in creating a risk class. This ensures the doctor would receive the current health status of the patient.

Figure 2:
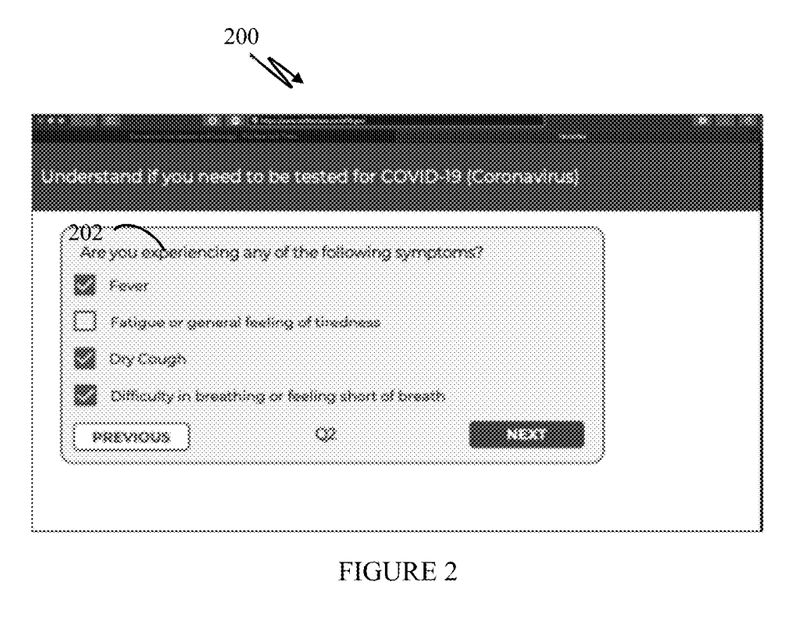
FIG. 2 illustrates an exemplary embodiment of the system for monitoring patient's health, in accordance with an embodiment of the present subject matter.

Referring now to FIG. 2, an exemplary embodiment 200 for a system for monitoring patient's health is shown, in accordance with an embodiment of the present subject matter. In the exemplary embodiment, construe Rajiv as a patient. Rajiv may use a user device. Rajiv is nudged with multiple questions. Rajiv have selected English as a language for questions. The question is 202—Are you following any of the following symptoms? Options—Fever, Dry cough, Fatigue or general feeling of tiredness, and Difficulty in breathing or feeling short of breathing. Rajiv selects the answers such as Fever, Dry cough, and Difficulty in breathing or feeling short of breathing. The system 102 receives the answer from Rajiv. Further, the answers are analyzed using a Natural Language Processing.

Upon analysis, a plurality of symptoms such as Fever, Cough, Difficulty in breathing, Night Sweats, Hemoptysis, Loss of smell or taste, Head ache and Body ache may be extracted. The plurality of symptoms is used to determine a health assessment score. The health assessment score is determined as 18. The health assessment score is compared with a predefined threshold to determine a health condition. The predefined threshold is 15. Further, the health condition as Covid-19 is determined. Furthermore, a deviation is determined. The deviation includes an increase in fever and body pain. Based on the deviation, a risk level may be identified. The risk level is a high risk. The system 102 recommends a course of action as visit to doctor or health practitioner. Further, a health care practitioner is identified for Rajiv based on the deviation and risk level. The health care practitioner is a covid specialist doctor working at a covid center hospital. Further, the system 102 notifies Rajiv and the health care practitioner. Upon notifying, the system 102 schedules a visit and a follow-up check for Rajiv.

Figure 3:
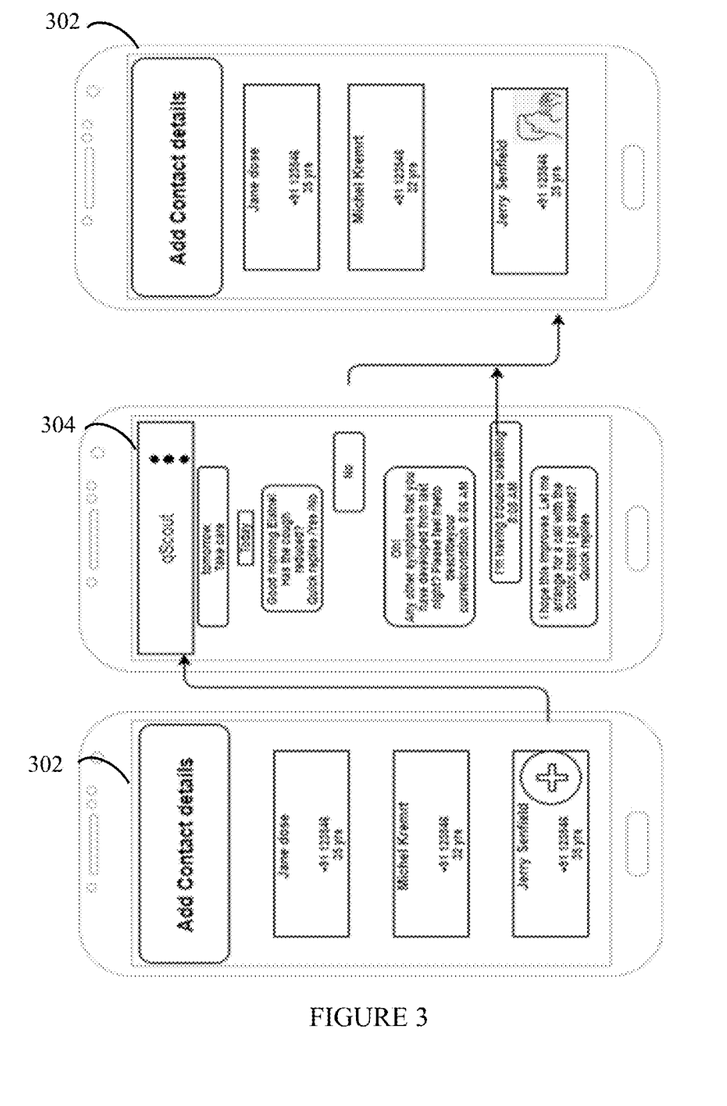
FIG. 3 illustrates an embodiment of the system for monitoring patient's health, in accordance with an embodiment of the present subject matter.

Referring now to FIG. 3, an embodiment of a system for monitoring patient's health, in accordance with an embodiment of the present subject matter. In the embodiment, contact details of a set of patients may be onboarded on a monitoring module 302. The contact may include a contact number or a phone number of the patient. In one aspect, a new contact may be added to the monitoring module 302.

Further, an interacting module 304 may nudge multiple questions to the patient. The multiple questions may be nudged periodically. In one example, construe Aman as the patient. A contact number of Aman is added in the monitoring module 302. The interacting module 304 nudge Aman with multiple questions. Aman provide answers to the multiple questions. Based on an analysis of the answers, a plurality of symptoms, for Aman, are identified. The plurality of symptoms includes fever, nausea and joint pain. The plurality of symptoms is analyzed to generate a health assessment score for Aman. The health assessment score is generated as 12. The health assessment score i.e., 12 is then compared with a predefined threshold i.e., 10 to determine a health condition of Aman. The health condition is determined as Dengue. The health condition i.e., Dengue is compared with previous health data to determine a deviation. The deviation is zero i.e., 0. A risk level is identified as a moderate risk. Based on the risk level and the health condition, a course of action is recommended to Aman in real-time. The course of action is medicines for Dengue.

Once the course of action is recommended, the monitoring module 302 may be updated. The monitoring module 302 may display an image near the contact. The image may indicate the course of action. In one aspect, the image of stethoscope may indicate the course of action as the visit to the doctor. In another aspect, the image of medicine may indicate the course of action as the medicine for the health condition. In the example, the icon of a patient taking medicines is displayed near the contact number of Aman.

Figure 4:
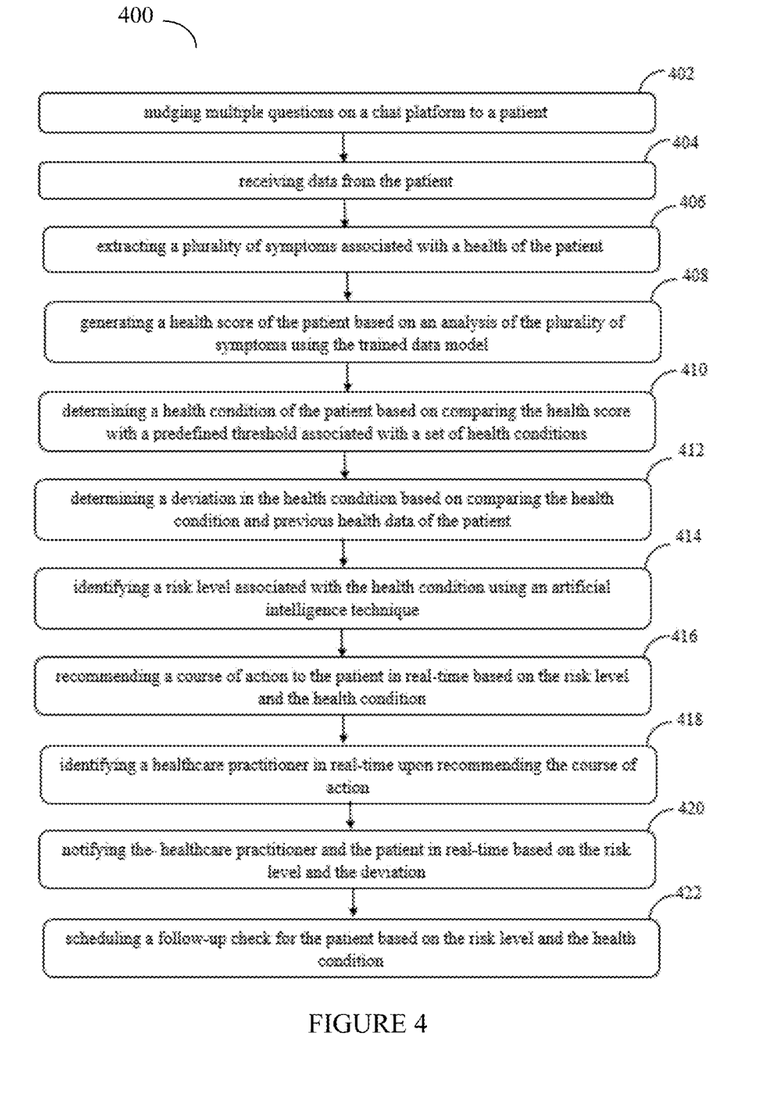
FIG. 4 illustrates a method for monitoring patient's health, in accordance with an embodiment of the present subject matter.

Referring now to FIG. 4, a method 400 for monitoring patient's health is shown, in accordance with an embodiment of the present subject matter. The method 400 may be described in the general context of computer executable instructions. Generally, computer executable instructions can include routines, programs, objects, components, data structures, procedures, modules, functions, etc., that perform particular functions or implement particular abstract data types.

The order in which the method 400 is described is not intended to be construed as a limitation, and any number of the described method blocks can be combined in any order to implement the method 400 or alternate methods for monitoring patient's health. Additionally, individual blocks may be deleted from the method 400 without departing from the spirit and scope of the subject matter described herein. Furthermore, the method 400 for monitoring the patient's health can be implemented in any suitable hardware, software, firmware, or combination thereof. However, for ease of explanation, in the embodiments described below, the method 400 may be considered to be implemented in the above-described system 102.

At block 402, multiple questions may be nudged on a chat platform to a patient. In one aspect, the multiple questions may be nudged dynamically. The multiple questions may be present in multiple languages. The nudge may be generated based on a trained data model.

At block 404, data may be received from the patient. In one aspect, the data may correspond to answers associated with the multiple questions asked to the patient. The data may be received periodically.

At block 406, a plurality of symptoms associated with a health of the patient may be extracted using a Natural language processing technique on the data.

At block 408, a health assessment score of the patient may be generated based on an analysis of the plurality of symptoms using the trained data model.

At block 410, a health condition of the patient may be determined based on comparing the health assessment score with a predefined threshold associated with a set of health conditions. In one aspect, the health condition may correspond to a disease.

At block 412, a deviation in the health condition may be determined based on comparing the health condition and previous health data of the patient. In one aspect, the previous health data may be stored in the trained data model.

At block 414, a risk level associated with the health condition may be identified using an artificial intelligence technique. In one aspect, the risk level may be identified based on the deviation and the plurality of symptoms. The risk level may be one of a high risk, a low risk and a moderate risk.

At block 416, a course of action may be recommended to the patient in real-time based on the risk level and the health condition. In one aspect, the course of action may comprise a visit to doctor, and treatment or medicine for the health condition of the patient.

At block 418, a healthcare practitioner may be identified in real-time upon recommending the course of action. In one aspect, the healthcare practitioner may be identified based on a demographic profile, the health condition, the risk level, a location of patient, a location of the healthcare practitioner, a distance between the patient and the healthcare practitioner, a traffic condition and a feedback associated with the health care practitioner received from a set of patients.

At block 420, the healthcare practitioner and the patient may be notified in real-time based on the risk level and the deviation.

At block 422, a follow-up check for the patient may be scheduled based on the risk level and the health condition. In one aspect, the follow-up check may be scheduled in a predefined time period, thereby monitoring patient's health.

Exemplary embodiments discussed above may provide certain advantages. Though not required to practice aspects of the disclosure, these advantages may include those provided by the following features.

Some embodiments of the system and the method enable virtual triage and contact tracing platform.

Some embodiments of the system and the method enable monitoring patient's health virtually.

Some embodiments of the system and the method enable monitoring patient's health within constraints of social distancing.

Some embodiments of the system and the method enable tracking, monitoring and managing patient's health using artificial intelligence technique.

Some embodiments of the system and the method enable remote follow-up for a patient with a health care practitioner.

Although implementations for methods and system for monitoring patient's health have been described in language specific to structural features and/or methods, it is to be understood that the appended claims are not necessarily limited to the specific features or methods described. Rather, the specific features and methods are disclosed as examples of implementations for monitoring the patient's health.

We claim:

1. A system to monitor patient's health, the system comprising:
a memory; and
a processor coupled to the memory, wherein the processor is configured to execute instructions stored in the memory to:
nudge multiple questions to a patient on a chat platform, wherein the multiple questions are nudged in real-time, and wherein the multiple questions are present in multiple languages, and wherein the nudge is generated based on a trained data model, and wherein the multiple questions are nudged in the real time based on patients' profile and medical history;
receive data from the patient, wherein the data corresponds to answers associated with the multiple questions asked to the patient, and wherein the data is received periodically;
extract a plurality of symptoms associated with a health of the patient using a Natural language processing technique on the data;
generate a health assessment score of the patient based on an analysis of the plurality of symptoms using the trained data model, wherein the health assessment score is generated based on a weightage of each symptom;
determine a health condition of the patient based on comparing the health assessment score with a predefined threshold associated with a set of health conditions, wherein the health condition corresponds to a disease;
determine a deviation in the health condition based on comparing the health condition and previous health data of the patient, wherein the previous health data is stored in the trained data model;
identify a risk level associated with the health condition using an artificial intelligence technique, wherein the risk level is identified based on the deviation and the plurality of symptoms, and wherein the risk level is one of a high risk, a low risk and a moderate risk;
recommend a course of action to the patient in real-time based on the risk level and the health condition, wherein the course of action comprises a visit to doctor, and treatment or medicine for the health condition of the patient;
identify a healthcare practitioner in real-time upon recommending the course of action, wherein the healthcare practitioner is identified based on a demographic profile, the health condition, the risk level, a location of patient, a location of the healthcare practitioner, a distance between the patient and the healthcare practitioner, a traffic condition and feedback associated with the health care practitioner received from a set of patients;

notify the healthcare practitioner and the patient in real-time based on the risk level and the deviation; and schedule a follow-up check for the patient based on the risk level and the health condition, wherein the follow-up check is scheduled in a predefined time period, and wherein the follow-up check is a physical follow-up or a remote follow-up, and wherein the follow-up check is scheduled using a supervised learning approach, and wherein the supervised learning approach comprises learning from past recommendations and actions taken by the patient, and wherein the past recommendations and the actions taken by the patient are stored in the trained data model, thereby monitoring patient's health.

2. The system as claimed in claim 1, further configured to generate an Electronic Medical Record (EMR) comprising the data, the health condition, the risk level and the course of action.

3. The system as claimed in claim 1, further configured to track a location of the patient to generate alert to the set of patients based on the risk level of the patient.

4. The system as claimed in claim 1, further comprises an adaptive risk engine to create schedulers linked to the disease and the follow-up check, wherein the adaptive risk engine determines the follow-up check based on co-morbidities of the patient.

5. A method for monitoring patient's health, the method comprising:

nudging, by a processor, multiple questions to a patient on a chat platform, wherein the multiple questions are nudged in real-time, and wherein the multiple questions are present in multiple languages, and wherein the nudge is generated based on a trained data model, and wherein the multiple questions are nudged in the real time based on patients' profile and medical history;

receiving, by the processor, data from the patient, wherein the data corresponds to answers associated with the multiple questions asked to the patient, and wherein the data is received periodically;

extracting, by the processor, a plurality of symptoms associated with a health of the patient using a Natural language processing technique on the data;

generating, by the processor, a health assessment score of the patient based on an analysis of the plurality of symptoms using the trained data model, wherein the health assessment score is generated based on a weightage of each symptom;

determining, by the processor, a health condition of the patient based on comparing the health assessment score with a predefined threshold associated with a set of health conditions, wherein the health condition corresponds to a disease;

determining, by the processor, a deviation in the health condition based on comparing the health condition and previous health data of the patient, wherein the previous health data is stored in the trained data model;

identifying, by the processor, a risk level associated with the health condition using an artificial intelligence technique, wherein the risk level is identified based on the deviation and the plurality of symptoms, and wherein the risk level is one of a high risk, a low risk and a moderate risk;

recommending, by the processor, a course of action to the patient in real-time based on the risk level and the health condition, wherein the course of action comprises a visit to doctor, and treatment or medicine for the health condition of the patient;

identifying, by the processor, a healthcare practitioner in real-time upon recommending the course of action, wherein the healthcare practitioner is identified based on a demographic profile, the health condition, the risk level, a location of patient, a location of the healthcare practitioner, a distance between the patient and the healthcare practitioner, a traffic condition and feedback associated with the health care practitioner received from a set of patients;

notifying, by the processor, the healthcare practitioner and the patient in real-time based on the risk level and the deviation; and scheduling, by the processor, a follow-up check for the patient based on the risk level and the health condition, wherein the follow-up check is scheduled in a predefined time period, and wherein the follow-up check is a physical follow-up or a remote follow-up, and wherein the follow-up check is scheduled using a supervised learning approach, and wherein the supervised learning approach comprises learning from past recommendations and actions taken by the patient, and wherein the past recommendations and the actions taken by the patient are stored in the trained data model, thereby monitoring patient's health.

6. The method as claimed in claim 5, comprises generating an Electronic Medical Record (EMR) comprising the data, the health condition, the risk level and the course of action.

7. The method as claimed in claim 5, comprises tracking a location of the patient to generate alert to the set of patients based on the risk level of the patient.

8. The method as claimed in claim 5, further comprises an adaptive risk engine to create schedulers linked to the disease and the follow-up check, wherein the adaptive risk engine determines the follow-up check based on co-morbidities of the patient.

9. A non-transitory computer program product having embodied thereon a computer program for monitoring patient's health, the computer program product storing instructions, the instructions comprising instructions for:

nudging multiple questions to a patient on a chat platform, wherein the multiple questions are nudged in real-time, and wherein the multiple questions are present in multiple languages, and wherein the nudge is generated based on a trained data model, and wherein the multiple questions are nudged in the real time based on patients' profile and medical history;

receiving data from the patient, wherein the data corresponds to answers associated with the multiple questions asked to the patient, and wherein the data is received periodically;

extracting a plurality of symptoms associated with a health of the patient using a Natural language processing technique on the data;

generating a health assessment score of the patient based on an analysis of the plurality of symptoms using the trained data model, wherein the health assessment score is generated based on a weightage of each symptom;

determining a health condition of the patient based on comparing the health assessment score with a predefined threshold associated with a set of health conditions, wherein the health condition corresponds to a disease;

determining a deviation in the health condition based on comparing the health condition and previous health data of the patient, wherein the previous health data is stored in the trained data model;

identifying a risk level associated with the health condition using an artificial intelligence technique, wherein the risk level is identified based on the deviation and the plurality of symptoms, and wherein the risk level is one of a high risk, a low risk and a moderate risk;

recommending a course of action to the patient in real-time based on the risk level and the health condition, wherein the course of action comprises a visit to doctor, and treatment or medicine for the health condition of the patient;

identifying a healthcare practitioner in real-time upon recommending the course of action, wherein the healthcare practitioner is identified based on a demographic profile, the health condition, the risk level, a location of patient, a location of the healthcare practitioner, a distance between the patient and the healthcare practitioner, a traffic condition and feedback associated with the health care practitioner received from a set of patients;

notifying the healthcare practitioner and the patient in real-time based on the risk level and the deviation; and scheduling a follow-up check for the patient based on the risk level and the health condition, wherein the follow-up check is scheduled in a predefined time period, and wherein the follow-up check is a physical follow-up or a remote follow-up, and wherein the follow-up check is scheduled using a supervised learning approach, and wherein the supervised learning approach comprises learning from past recommendations and actions taken by the patient, and wherein the past recommendations and the actions taken by the patient are stored in the trained data model, thereby monitoring patient's health.

* * * * *